US00PP09301P

United States Patent [19]

Dehan

[11] Patent Number: Plant 9,301

[45] Date of Patent: Sep. 26, 1995

[54] GYPSOPHILA PLANT NAMED 'MAGIC TAVOR'

[75] Inventor: Klara Dehan, Holon, Israel

[73] Assignee: Danziger "Dan" Flower Farm, Post Beit Dagan, Israel

[21] Appl. No.: 299,615

[22] Filed: Sep. 2, 1994

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 8,352 8/1993 Zemach ..... Plt./68.1

P.P. 8,652 3/1994 Dehan ..... Plt./68.1

*Primary Examiner*—James R. Feyrer

*Attorney, Agent, or Firm*—Foley & Lardner

[57] ABSTRACT

A new and distinct cultivar of gypsophila plant named Magic Tavor, characterized by its white flower color, sturdy stems, upright and conical growth habit, floriferousness, early flowering, continuous flowering in Israel from April to late fall, and its suitability for cut flower production.

1 Drawing Sheet

The present invention relates to a new and distinctive cultivar of Gypsophila plant, referred to by the cultivar name Magic Tavor.

The new cultivar was developed by the inventor Klara Dehan in Mishmar Hashiva, Israel through controlled breeding by crossing male and female parents which are unknown at this time. Both parents were selected seedlings from the breeding of grandparents which are likewise unknown at this time. Both the parent and grandparent cultivars are proprietary lines used exclusively for breeding.

Asexual reproduction by leaf cuttings taken by the inventor at Mishmar Hashiva, Israel has shown that the unique features of this new gypsophila are stabilized and are reproduced true to type in successive propagations.

The following characteristics in combination distinguish the new gypsophila from other cultivated gypsophila of this type known and used in the floriculture industry:

1. Round flower form.
2. White flower color.
3. Flowers are carried on relatively long sturdy stems.
4. Floriferous habit, with many flowers being in bloom and bud at one time.
5 . The growth habit of Magic Tavor is generally upright and conical, with the side branches being relatively close to the main stem. The new cultivar is therefore particularly suited for cut flower reproduction.
6. Excellent branching, particularly if the plant is pinched 3–5 weeks after planting.
7. In Mishmar Hashiva, Israel, the new cultivar flowers continuously from approximately April through late fall.
8. Magic Tavor possesses day neutrality that is, it will respond to lower levels of light for flowering. Thus, under natural outdoor light conditions, the new cultivar will flower comparatively earlier in the spring and very late in the fall or early winter.

The accompanying colored photograph illustrates the branching and flowering traits of Magic Tavor, showing the colors as true as it reasonably possible to obtain in colored reproduction of this type.

The new cultivar can be compared in certain traits to the unpatented cultivar Perfecta, a commercial cultivar well known in Israel. With regard to flowering, when grown under the same temperatures and day length, Magic Tavor will reach flowering faster, particularly in the spring and fall, due to the ability of Magic Tavor to induce flowering under shorter day lengths. For example, in November with a day length of 10.5 hours in Israel, Magic Tavor will flower and Perfecta will not. Magic Tavor produces about 25% fewer flowering stems per flash than Perfecta, under the same growing conditions.

The following is a detailed description of the new cultivar based on plants produced in an open filed in accordance with commercial practices in Mishmar Hashva, Israel.

Color references are made to the Royal Horticultural Society Colour Chart (RHS) except where general terms of ordinary dictionary significance are used.

Parentage: Both male and female parents are unknown.

Propagation: By leaf tip cuttings, rooting is very good, with roots being initiated in 10–11 days at 30° C. in summer, and in 11–12 days at 20° C. in winter.

PLANT DESCRIPTION

A. Form: Upright and conical, excellent for cut flower production.

B. Habit of growth: Fast growing and excellent branching. When grown in Israel under average winter temperatures of approximately 10° C. and under normal field conditions, the height of the new cultivar is approximately 75 cm. Flowering is early since Magic Tavor has been shown to have day neutrality that is, it is less responsive to daylength than some other cultivars in this class. The plant is perennial in Israel where average winter temperatures are approximately 10° C.

C. Foliage:

1. *Size.*—Leaves are long and narrow, approximately 12 cm in length and 1.5 cm in width; there are very few leaves on flowering stems.
2. *Shape.*—Lanceolate.
3. *Margin.*—Entire.
4. *Texture.*—Hairy.
5. *Color.*—Top side: 147A. Under side: 147A.
6. *Venation.*—Palmate but very inconspicuous with a prominent midrib.

FLOWERING DESCRIPTION

A. Natural flowering season: In Israel under outdoor conditions, flowering starts in April and continues until late fall.

B. Flower buds: Closed bud is round and approximately 2 mm in diameter.

C. Flowers borne: On relatively long, rigid stems.

D. Quantity of flowers: Very floriferous; a total of approximately 2000 flowers are produced on one flowering stem.

E. Petals:

1. *Shape.*—Generally round.
2. *Color.*—155D, fading to very pale pink.
3. *Number of petals.*—Approximately 20–25.
4. *Size of flowers.*—Approximately 1.0 cm in total flower diameter.

F. Reproductive organs: Flowers are monoecious.

1. *Stamens.*—5 anthers, thin, color white; pollen is white.
2. *Pistils.*—Stigma are cone shaped and light green in color; style is light green; there are five ovaries 1.2 mm in size and light green in color.

G. Disease resistance: Magic Tavor has not been shown to be sensitive to botrytis or other common diseases.

H. Fertility: male and female sterile.

I claim:

1. A new and distinct cultivar of gypsophila plant named Magic Tavor, as illustrated and described.

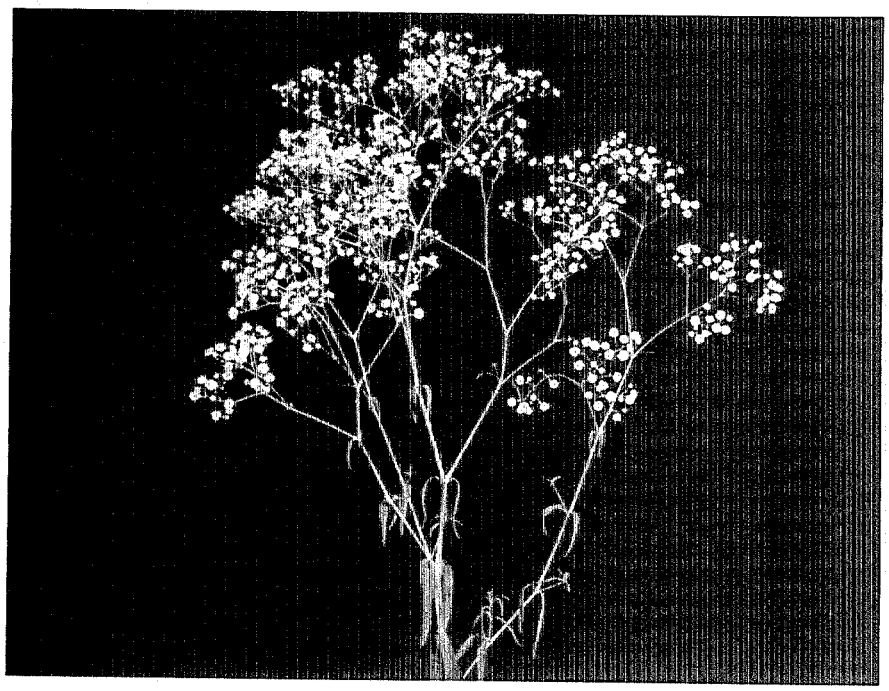

* * * * *